United States Patent [19]

Gevins

[11] Patent Number: 5,295,491
[45] Date of Patent: Mar. 22, 1994

[54] NON-INVASIVE HUMAN NEUROCOGNITIVE PERFORMANCE CAPABILITY TESTING METHOD AND SYSTEM

[75] Inventor: Alan S. Gevins, San Francisco, Calif.

[73] Assignee: Sam Technology, Inc., San Francisco, Calif.

[21] Appl. No.: 766,826

[22] Filed: Sep. 26, 1991

[51] Int. Cl.⁵ ............................................. A61B 5/0482
[52] U.S. Cl. ..................................... 128/731; 128/732
[58] Field of Search ......................... 128/731, 732, 791

[56] References Cited

U.S. PATENT DOCUMENTS

| 740,385 | 10/1903 | Bassell | 128/791 |
| 3,901,215 | 8/1975 | John | 128/731 |
| 4,913,160 | 4/1990 | John | 128/731 |
| 4,987,903 | 1/1991 | Keppel et al. | 128/731 |

Primary Examiner—William E. Kamm
Assistant Examiner—Scott M. Getzow
Attorney, Agent, or Firm—Eliot S. Gerber

[57] ABSTRACT

A testing method and system for testing the mental performance capability of a human subject includes a digital computer workstation which presents a test to the subject, such as visumotor memory task. Simultaneously, a physiological sensing and amplification device amplifies and analyzes the subject's brain waves, eye activity, scalp and facial muscle activity, heart activity, respiration and/or skin conductance. The subject's test scores and physiological activity are compared, by the workstation, with previously collected normative measurements for that subject to determine if the test was passed with a passing score and, if so, whether the subject, in order to pass the test, exceeded a standard based upon the subject's normal mental effort in taking the same or similar tests.

22 Claims, 5 Drawing Sheets

NON-INVASIVE HUMAN NEUROCOGNITIVE PERFORMANCE CAPABILITY TESTING METHOD AND SYSTEM

This invention was made with government support under contract F49620-92-C-0013 awarded by the Air Force Office of Scientific Research. The Government has certain rights in the invention.

BACKGROUND OF THE INVENTION

1. Field of the Invention

The present invention relates to medical devices and methods for testing neurocognitive capability by measurements of humans using an EEG (electroencephalograph) and physiological function monitoring system.

2. Description of the Related Art

At the present time there is considerable interest in testing the performance ability of those engaged in certain types of work. For example, recently in New York City a subway train derailed because the motorman was drunk, killing passengers and shutting down a vital subway line for a week.

The issue of safety is of prime importance in many activities, such as public transportation and nuclear plant operation. There is a widespread concern of increased instances of substance abuse, including the use of cocaine, alcohol, etc., by those entrusted with the safe operation of public vehicles such as airplanes, railroads and buses, as well as those who operate facilities which require a high degree of attention, such as nuclear power plants, chemical plants and military facilities.

A program of random drug and alcohol testing has been suggested and in some cases implemented. However, those tests, since they test only a few employees each week, may overlook those employees whose performance sometimes fails, but whose performance does not fail regularly. That type of program may be resisted as being intrusive into the employee's life, since it may involve a blood and urine test.

A performance type of testing program has recently been tried in a few transportation systems in which each employee, before he/she starts work, takes a simple eye-hand coordination test using a digital computer having a screen. For example, a spot is randomly shown on the screen and the person being tested has to move the cursor, using a mouse input device, to cover the spot. This type of performance testing has generally been accepted by employees and their unions because it is non-invasive and seems to be objective.

Performance testing has important advantages over chemical testing:

(i) It detects worker impairment before the employee goes on the job. Chemical testing does not;

(ii) Performance testing discovers impairment for any reason (for example, a hangover or anxiety about a sick child). Chemical testing does not; and (iii) Performance testing is cheaper than chemical testing and less invasive. While workers commonly resent chemical testing (often having to urinate in a cup in front of witnesses), the majority do not mind performance testing.

Performance testing is gaining acceptance as the preferable method for workers in sensitive positions like train drivers. However, performance testing has the basic fault that it passes some employees who should not be allowed to go to work. For example, a partially drunk employee, or one partially high on drugs, or one over-fatigued, may pass the test by concentrating on the test. When a person places his/her concentration on passing a short eye-hand coordination test, in many cases the test will be passed, although the person would otherwise fail and should not be allowed to work in a position where safety is important.

OBJECTIVES AND FEATURES OF THE INVENTION

It is an objective of the present invention to provide a method and system for the testing of humans which will test their real physiological capability to perform a task without being misled by the subject's concentration on passing the test.

It is a further objective of the present invention that the test be non-invasive and may be taken relatively quickly, so that the test may be administered to each employee before he/she begins to work.

It is a further objective of the present invention to detect the subject's substance abuse, fatigue or illness before he/she starts to work or during the work period.

It is a feature of the present invention to provide a method and system to determine the cognitive or mental performance capacity of a human subject to perform a work assignment, such as driving a bus or piloting an airplane. Neurocognitive tests are used to greatly enhance the sensitivity of the system. The term "neurocognitive" refers to those mental functions for which physiological indices can be measured. The subject is first given a series of performance tests, while the subject is sober and alert, to obtain a normative test score for the subject, and that normative test score is recorded in a digital computer workstation. Simultaneously with those tests, the brain waves and/or other physiological signals such as eye movements or blinks, heart activity, respiration, muscle activity and skin conductance of the subject are detected and analyzed. Brain waves are detected by an EEG (electroencephalograph) having a plurality of electrodes removably connected to the scalp of the subject. Other physiological signals are detected by a physiological signal recording device having electrodes or other sensors connected to appropriate parts of the body of the subject. The computer system analyzes the EEG and other signals to determine a normative neurocognitive capacity score for the subject (the normal neurocognitive capacity utilized by the subject to obtain the normative test score). That normative neurocognitive capacity score is also recorded in the computer workstation. The normative neurocognitive capacity score can optionally be a weighted function of both the performance test scores and the EEG and other physiological signals. This allows a combination of performance test scores and EEG or physiological signals into a single more sensitive index. Subsequently, preferably before the subject begins work each day, the subject is tested in a test of performance of a task to obtain a test score. The workstation compares the test score with the normative test score. If the test score is too low (below a passing grade) the subject is not permitted to go to work that day or should be placed in another work situation which does not involve safety considerations. Simultaneously with the daily test, the subject's brain waves are detected and analyzed with an EEG (electroencephalograph) device having a plurality of electrodes removably connected to the scalp of the subject, and/or the other physiological signals are also appropriately recorded, to determine the neurocognitive capacity the subject used to take the test. The workstation then compares the neurocognitive capacity used by the subject with the subject's normative neurocognitive capacity score. Consequently the subject is rejected (the subject is not allowed to perform the work assignment) if the subject's test score is a predetermined passing score below the normative test score or if the subject's test score is above said passing score; but the subject requires excessive neurocognitive capacity, as determined in the brain wave and physiological signal comparison, to obtain the passing score.

It is a further feature of the present invention that (i) the subject is tested each day prior to the subject's work assignment; (ii) if fatigue on the job is a safety factor the subject is tested at least twice each work day; (iii) the subject wears a hat having a plurality of electrodes to contact the scalp and face of the subject with attachments to the hat for measuring eye, muscle, heart, respiration and skin conductance activity; (iv) the tests are visumotor memory task and/or the other tests of attentional capacity, working memory, perceptuomotor coordination, short-term memory, spatial reasoning, logical reasoning and calculation which comprise the Neurocognitive Functional Analysis battery. The tests are displayed on the screen of a digital computer system or presented by a speaker controlled by the computer system; and (v) the subject responds to the tests by operation of a keyboard, joystick, or pressure key connected to the computer system.

It is a further feature of the present invention that a subject's normative test score and normative neurocognitive capacity score are improved as more data becomes available. Normally a subject becomes familiar with the tasks and practices them before determining his/her normative test score and normative neurocognitive capacity score. In an optional mode of operation, data from two or more practice tests are used to mathematically model the subject's learning characteristics, reducing the need for more extensive practice tests and resulting in a more sensitive and accurate test.

It is a further feature of the present invention that in comparing a subject's test score and neurocognitive capacity score with their normative test and neurocognitive capacity scores, use can optionally be made of group normative and impaired test scores and group normative and impaired neurocognitive capacity scores to improve the sensitivity and specificity of the system. This is done by customizing to the subject the generic functions which distinguish normal from impaired mental functioning. As more data is accumulated from a subject, the selection of the generic functions becomes more specific to the subject.

SUMMARY OF THE INVENTION

In accordance with the present invention a system and method is provided for the testing of human subjects to assure their capability of performance.

The subject is tested, preferably before beginning his/her work period. In addition, or alternatively, especially for situations such as nuclear power plants, in which fatigue is a problem, the subjects may be tested during their work periods.

The test uses a digital computer workstation having a screen and an input device, an EEG (electroencephalograph) to measure the brain waves of the subject, and sensors and amplifiers to measure eye activity, scalp and facial muscle potentials, heart activity, respiration and skin conductance. The subject is presented with a test, on the screen, which tests the basic cognitive and perceptuomotor functions used in the work he/she is to perform. For example, the test is a visumotor-memory task trial such as remembering a number and applying a finger pressure proportional to the remembered number to a pressure-sensitive key connected to the workstation. The subject's score is recorded and compared with previous scores obtained by the same subject, in a number of trials, while the subject was sober, alert and healthy. Simultaneously, the subject's brain waves and other physiological signals are detected and measured, preferably using an easily removable hat or helmet having a plurality of electrode or sensor leads. The brain waves and other physiological signals, which are weak analog signals, are amplified and converted into digital form for subsequent automatic analysis by the computer workstation.

The computer workstation, using suitable computer software, compares the subject's brain waves and other physiological signals to a set of standards previously derived from the same subject, in a series of trials, while he/she was sober, and alert, and healthy.

If the subject fails the test, i.e., his/her scores are too low or if the subject passes the test but requires too much neurocognitive effort (as indexed by changes in the EEG and/or other physiological signals) to pass the test, then the subject is not allowed to go to work that day, or to continue working.

BRIEF DESCRIPTION OF THE DRAWINGS

Other objectives and features of the present invention will be apparent from the following detailed description, taken in conjunction with the accompanying drawings. In the drawings.

DETAILED DESCRIPTION OF THE INVENTION

Figure 1A:
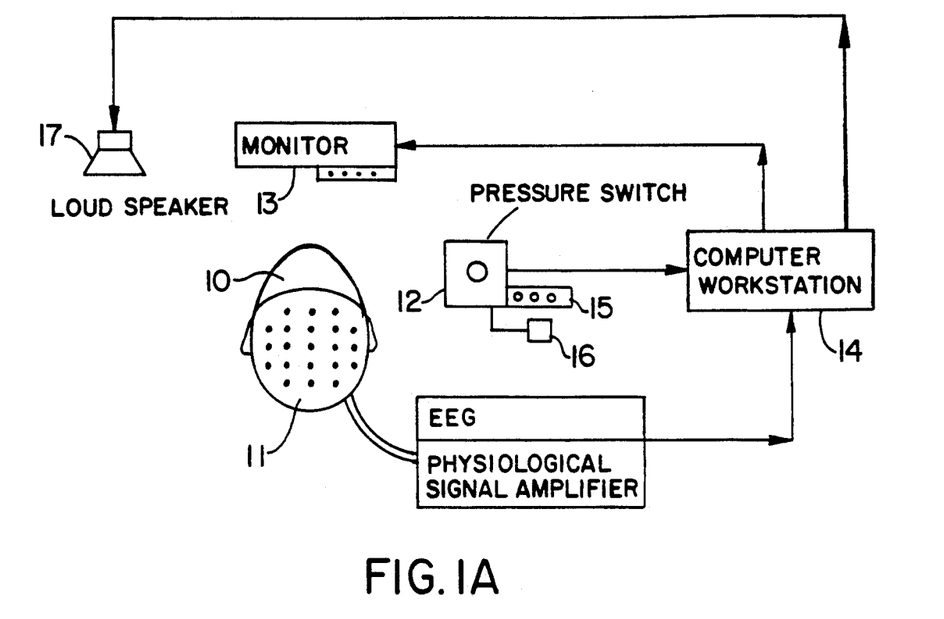
FIG. 1A is a schematic diagram of the system of the present invention.

The present invention is illustrated in FIG. 1A. As shown therein, a human subject 10, whose head is illustrated, wears a nylon mesh hat or helmet having electrode leads which contact the scalp of the subject. The leads detect the subject's weak analog brain waves and also the electrical activity of their eyes and scalp muscles. Electrodes or other sensors connected by wires to the hat attach to the face, neck, chest, back or limbs to record other physiological signals including eye, facial muscle, respiration or heart activity and skin conductance. A suitable EEG hat is described in the inventor's U.S. Pat. No. 5,038,783, issued Aug. 13, 1991 and incorporated by reference herein. The hat has preferably 19-56 independent electrodes, although fewer or more electrodes may be used. The brain waves are amplified, preferably as described in the U.S. Pat. No. 5,038,783, and artifacts detected and removed, for example, as described in U.S. Pat. No. 4,736,751, issued Apr. 12, 1988 and entitled "Brain Wave Source Network Location Scanning Method And System", incorporated by reference herein.

Other physiological signals are detected and measured, for example, as follows: Eye movements and blinks are measured with EEG electrodes placed near the eyes, preferably above and below one eye for vertical movements and blinks, and on the nasion and outer cathus of one eye for horizontal movements (electroculogram or EEG). The amplifier response to such eye movements and blinks is similar to that for EEG, except that gain is reduced by a factor of 20 to 50. Alternatively, eye movements and blinks may be measured with an optoelectric device which measures the reflection of infrared light from the margins between the iris and sclera o either side of the pupil.

Scalp or facial muscle potentials (electromyogram or EMG) are measured with EEG electrodes placed over scalp muscles or on the face, with a bandpass of from approximately 36 to 100 Hz. Heart activity (electrocardiogram or ECG) is measured with conventional EEG electrodes placed appropriately on the upper chest, limbs or neck. Amplifier response is similar to that for EEG, except that gain is reduced by a factor of 5 to 10. Skin conductance response (SCR) is obtained from the voltage generated by an alternating current of roughly 10 microamps run through two electrodes placed appropriately on the subject's forehead, fingers, palm, or armpit. Amplifier response is similar to that for EEG, except that gain is reduced by a factor of 50 to 100. Respiration is measured by a nasal thermistor or an electrically resistive stretch device placed around the upper chest. Changes in resistance are indicated by the amplified output of a bridge circuit with a regulated voltage input.

Simultaneously with the detection of the subject's brain waves and other physiological signals, the subject is presented with a test, preferably on the screen 13 of a CRT monitor, or by a loudspeaker 17 connected to the digital computer workstation 14. The subject regards the monitor screen or listens to the loudspeaker and responds using a pressure sensitive switch 12, or alternatively a keyboard 15 or a joystick 16. An example of a visumotor memory test is set forth in detail below.

The test scores of the individual are taken over a series of times when the subject is, by professional observation, deemed to be sober, alert and healthy. This provides a performance test score standard ("normative test score") for the individual. If the subject fails the performance test, given, for example, each time the subject reports to work, then the subject should not be allowed to go to work or should be placed in a work situation which does not involve safety considerations.

An optional feature of all tests is that their difficulty is automatically increased as a subject's performance improves as a result of practice. This is done by decreasing the maximum time allowed for a response by the subject, and also by making the task problem harder to solve, for example, by requiring that more items be remembered. When this is done, the difficulty level of the task is used along with the correctness and speed of the subject's response in determining his/her normative test score.

But even if the subject passes the performance test, with a score that is within a predetermined amount of the subject's normative test score, the subject may not be fit to go to work because the subject required too much of the subject's mental effort to pass the test. The subject's normal mental effort, while taking performance tests, is measured, while the subject is alert, sober and healthy. That series of measurements forms a normative neurocognitive capacity score for that person. If the subject uses too much neurocognitive capacity (above a score based upon the normative capacity score for that person) in order to pass the performance test, the subject should be rejected from going to work which involves safety considerations.

In addition to fixed values for the normative test score and the normative neurocognitive capacity score, an optional feature of the system is that the normative test score and the normative neurocognitive capacity score are updated each time after the subject successfully passes the test.

The normative test score and the normative neurocognitive capacity score for a subject are obtained preferably over a series of tests taken over a number of days. Such testing is readily accomplished if the subject is an employee who reports for work each day. However, for example in a medical setting, the patient may take a medical examination only once a year, or even less frequently. It is useful to use group normative test scores and group normative neurocognitive capacity scores based on testing of groups of subjects of similar age, education, nationality (for language based tests) and sex. Such group test scores may then be combined with the subject's actual test scores (based on one or a few tests) to provide combined normative scores for the subject, without extensive repeated testing of the subject. For example, a patient may take the tests twice during the subject's initial visit to a medical facility. That initial testing session would provide data which is combined with the group normative scores, from a group having similar age, sex and education as the subject. When the subject next visits the medical facility, for example, a year later, his/her actual scores are compared with the combined normative scores as an indication of whether the subject's neurocognitive capacity score has changed and, if so, whether it has improved or declined.

A detailed description of one type of test, a visumotor memory task trial, is set forth below. Alternatively, or in addition, other types of performance tests may be used. Other types of tests, and an example of each type, is as follows.

Mathematical processing tests subjects' ability to perform simple arithmetic operations. A summation problem with at least three operands and two or more of the four operators indicating addition, subtraction, multiplication or division is presented. The subject judges whether the answer is true or false.

A test of logical reasoning tests subjects' ability to perform simple reasoning. A statement and two or more propositions are presented: e.g., "zyx", "x after y", and "y before z", respectively. The subject indicates whether or not all the propositions have the same truth value. A test of Spatial Processing tests subjects' ability to perform mental rotation and visual matching. Two bar charts, consisting of at least 3 bars of varying height, appear successively. First, a vertical bar chart appears; this is replaced by a horizontal bar chart with a leftward or rightward tilt. The subject determines whether or not the second bar chart is a rotated version of the first.

A test of memory search tests an aspect of immediate memory. A group of at least three letters or numbers are presented. This followed by a series of single letter or number probes presented one by one. For each of these, the subject determines whether or not they were in the group.

A test of visuomotor tracking tests visuomotor coordination and attention. Subjects try to keep a horizontally moving cursor centered on a target in the middle of a screen by using a joystick or depressing one key for leftward movement and another key for rightward movement. A positive feedback control system magnifies any deviation of the cursor from the target. The stability of the system is decreased gradually. A trial terminates when the subject loses control and the cursor crashes into either a left or right boundary displayed on the screen.

A test of divided attention tests subjects' ability to effectively allocate attentional resources to two independent tasks. This task consists of combining the Memory Search task with the Visuomotor Tracking task. One hand is used for tracking while the other responds to the Memory Search probes. The group of letters or numbers is shown before tracking begins. After a short warm-up on the tracking task, the shape of the cursor changes to a probe letter or number of the Memory Search task. A new probe is shown immediately following a response by the appropriate hand.

A test of short term memory tests subjects' ability to remember words over an interval of roughly 3 to 5 minutes. At the beginning of performing a battery of tests, subjects are shown a series of monosyllabic words, one at a time. After performing a number of other tests, the subject is shown a series of probe words one at a time. The subject determines whether or not a word had been previously presented.

A test of word scrambling tests subjects' ability to manipulate symbols and access long-term memory. Subjects are presented a string of at least three letters. Subjects determine whether or not the letters can be unscrambled to form an English word.

A test of N-back working memory tests subjects' ability to continuously update working memory. Subjects are presented a series of images or words, one at a time. To each stimulus, subjects determine whether or not the stimulus matches the stimulus that preceded the last $N-1$ stimuli.

A test of N-back divided attention tests subjects, ability to continuously update working memory in addition to performing higher order operations, e.g., language and mathematical processing. Subjects are presented a series of stimuli, one at a time. To each stimulus, subjects must perform an operation between the present stimulus and the stimulus that preceded the last $N-1$ stimuli. Example stimuli and operations are 1) words, subject determines if a pair of words are symantically equivalent; 2) words, subject determines if a pair are antonyms; 3) digits, subject determines whether or not the differences between a pair is greater than or less than five, etc.

A test of attentional flexibility tests subjects' ability to quickly switch contexts for interpreting information. A cue, either "same" or "opposite", is presented at the center of the screen, followed by a digit between 0 and 9 to either the right or left of the cue. The cue "same" directs the subject to respond with the hand on the same side as that of the digit stimulus; "different" directs the subject to use the opposite hand. The subject responds with a lower left or right key if the digit is less than five; otherwise, the correct response is an upper left or right key.

The following description is of an experiment directed to the effect of fatigue o subjects using visumotor memory task trials. However, the final effect of fatigue, as determined by EEG and other physiological measurements, may be the same as other causes of lack of ability to perform safely.

Methods of the Experiment

Subjects and Task

Each of 5 healthy, right-handed male Air force jet test pilots practiced a battery of 4 tasks for about 6 hours until the learning curves for responses error stabilized. Subjects began at about 1:30 p.m. the following day, and during the ensuring 10-14 hours performed several types of tracking and cognitive tasks, including about 1400 visuomotor memory task trials. The session consisted of a 5-8 hour work period, a brief dinner break, then another 5-7 hours work period which ended when the subject was too exhausted to continue.

Visuomotor memory task trials were presented in blocks of 50. Except for the first 2 trials in the block, subjects produced a precise finger pressure proportional to a number seen 2 trials back (about 11.5 sec earlier). Each trial began with the disappearance of the letter X from the video screen. A single-digit stimulus number, which the subject was required to remember, appeared 750 msec later. Stimuli were presented for 325 msec on a Videographic-II amber CRT monitor 70 cm from the subject. Stimuli subtended a visual angle under 1.5°, with an illumination of $cd/m^2$. When the stimulus number disappeared, the subject was required to produce a pressure of 0.1-0.9 kg with his right index finger on an isometric pressure transducer. The appropriate response pressure corresponded to the stimulus number presented 2 trials earlier. For example, if the stimulus numbers in 4 successive trails were 3, 7, 6 and 9, the correct responded would be 0.3 kg to the 6 and 0.7 kg to the 9 (FIG. 1). A two-digit feedback number was presented in each trial 1 sec. after the peak of the response to indicate the actual pressure exerted. The feedback number was underlined if the response was close to the required response, based on an 'adaptive error tolerance', computed as the geometric mean of the response error (distance from the required pressure response) on the previous 5 trials.

To increase the difficulty, the subject was required to withhold his response in the approximately 20% of the trials when the stimulus number was the same as the number from 2 trials back. For example, if the numbers 6, 9, 6 were presented, the subject was not to respond to the second 6 (FIG. 1B).

Figure 1B:
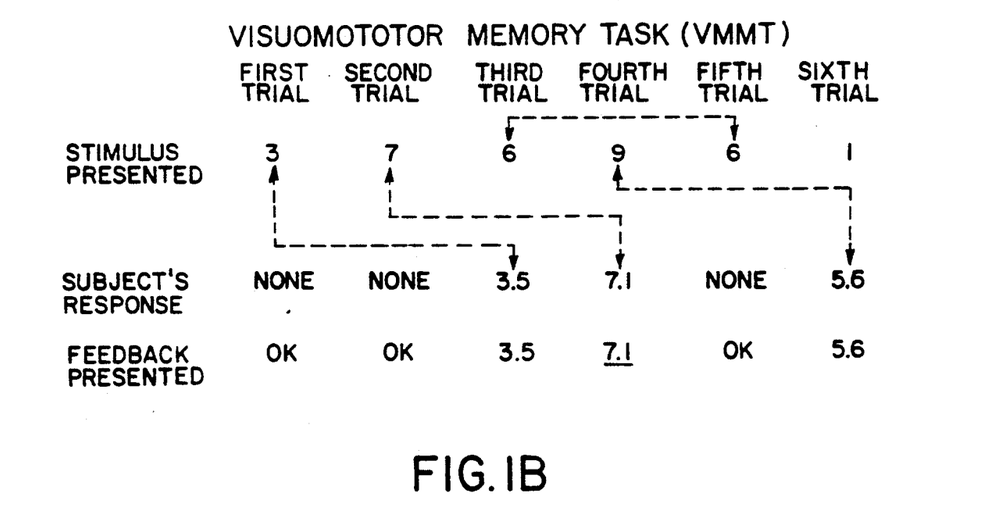
FIG. 1B is a diagram of the visumotor memory task.

As shown in FIG. 1B, the visuomotor memory tasks (VMMT) required that subjects remember, during each trial, a stimulus number from 2 trials back and produce a precise right index finger pressure in response to that number. Each trial consisted of a warning disappearance of the letter X from the video screen—not shown), followed 0.75 sec later by presentation of a single-digit visual stimulus to be remembered, followed by the subject's finger-pressure response to the stimulus number presented 2 trials back, followed 1 sec after the peak of the response by presentation of a 2-digit feedback number indicating the accuracy of the response. The feedback number was underlined when the subject's response was highly accurate. Subjects were required to withhold their response when the current stimulus number was identical to the stimulus 2 trials back. No response was required on the first 2 trials of each block of 50 trials -signified by 'OK'.

Recording

Neuroelectric data were recorded from an array of electrodes built into a nylon mesh hat. Signals were recorded from 27 electrodes and were referenced to the right mastoid. All signals were amplified by a Bioelectric Systems Model AS-64F with 0.016-50 Hz passband and digitized to 11 bits at 128 Hz. Vertical and horizontal eye movements (VEO, HEO), activity of the right flexor digitorum muscle (EMG), cardiac rate (EKG), respiration, and EEG activity at left mastoid were recorded from all subjects. Two technicians, working independently, edited the time-series traces off-line and eliminated data with evidence of contamination by potentials generated by eye movements, muscle activity, or instrumental noise sources. An optimal, least-squares estimate of the Laplacian operator was computed to reduce spatial low-pass distortion resulting from transmission through the skull and scalp. Electrodes at the edge of the array were eliminated from the analysis because it is not possible to reliably estimate their Laplacian. Even though Laplacian-transformed potentials are proportional to current density, we will refer to those wave forms as potentials, in keeping with common usage.

Figure 2:
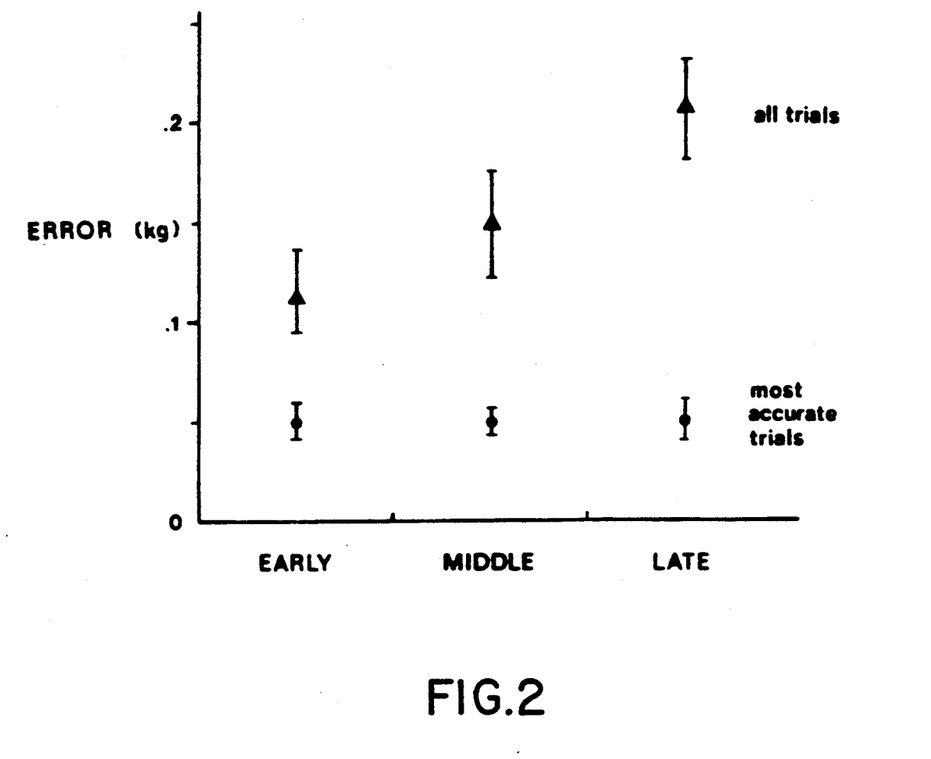
FIG. 2 is a sheet showing means and standard deviation of response error for Early, Middle and Late epochs. The upper set of points represents all finger-pressure trials, while the lower set is from the most accurate finger-pressure trials.

Recording sessions were divided into 3 epochs termed Early, Middle and Late based on response error (FIG. 2). Each epoch was long enough to allow us to form stable estimates of the functional brain patterns occurring during it. The Early epoch lasted approximately from 1:30 p.m. to 8:30 p.m., the Middle from 8:30 p.m. to 10:30 p.m., and the Late from 11:30 p.m. to 1:30 p.m.

Signal Analysis

ERCs, a statistical measure of functional interrelatedness between the time series of 2 channels, were computed from pre- and post-stimulus intervals of the task. Although the exact brain sources of scalp ERCs have not yet been determined, intracerebral recordings from animals and scalp recordings from humans suggest that ERC patterns reflect the coordinated, low-frequency task-related dendritic activity pattern of distributed cortical neuronal networks.

Figure 3A:
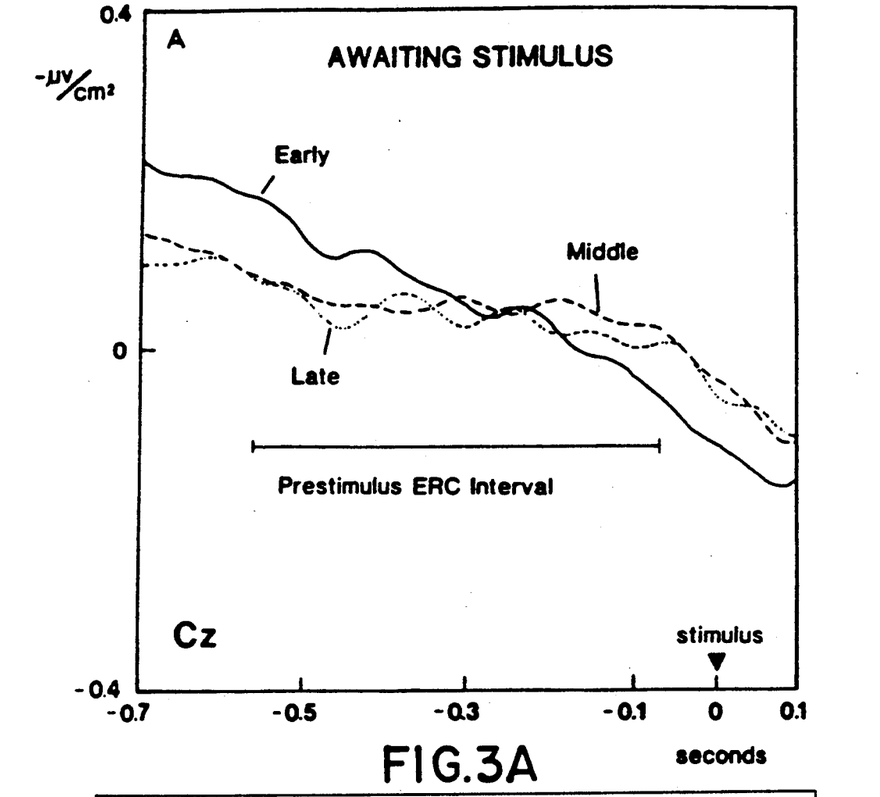
FIG. 3A is a chart showing a grand-average (over all 5 subjects) of event-related potential (ERP) laplacian wave forms at the midline central (Cz) electrode during a split-second time interval when the subjects stared at a blank screen while remembering two numbers. Early, Middle and Late refer respectively to data collected early in the day, after 6–8 hours of task performance, and after 10–14 hours of task performance.

ERCs were computed from bandpass-filtered event-related potentials (ERPs) time-locked to the presentation of the numeric stimulus, and averaged over the 5 subjects. Three well-known ERP waves were used as timing markers; the prestimulus CNV during the Finger-Pressure trials, the post-stimulus N1-F2 during stimulus processing on the Finger-Pressure trials and the post-stimulus F3 elicated during the infrequent No-Press trials. The pre-stimulus ERC interval was 500 msec wide and was centered 312 msec before the numeric stimulus (FIG. 3A). The 2 post-stimulus ERC intervals were 187 msec wide. The first was centered at 125 msec after the stimulus for Finger-Pressure trials (FIG. 4A), and the second at 375 msec for No-Press trials (FIG. 5A).

Bandpass filters were chosen to enhance the ERP waves of interest. Thus the pre-stimulus interval was filtered with a 0.01-3 Hz passband to emphasize the CNV, whereas a 4-7 Hz passband was selected for the post-stimulus intervals to accentuate the N1-F2 and F3 components. The cross-variance function was computed to 16 lags ($+/-$ 125 msec) for the 0.01-3 Hz-filtered intervals. The ERC was defined as the maximum absolute value of the lagged time series cross-covariance function. ERCs for the 3 intervals were computed between all 153 pairwise combinations of the 18 non-edge scalp electrodes common to all 5 subjects.

Figure 3B:
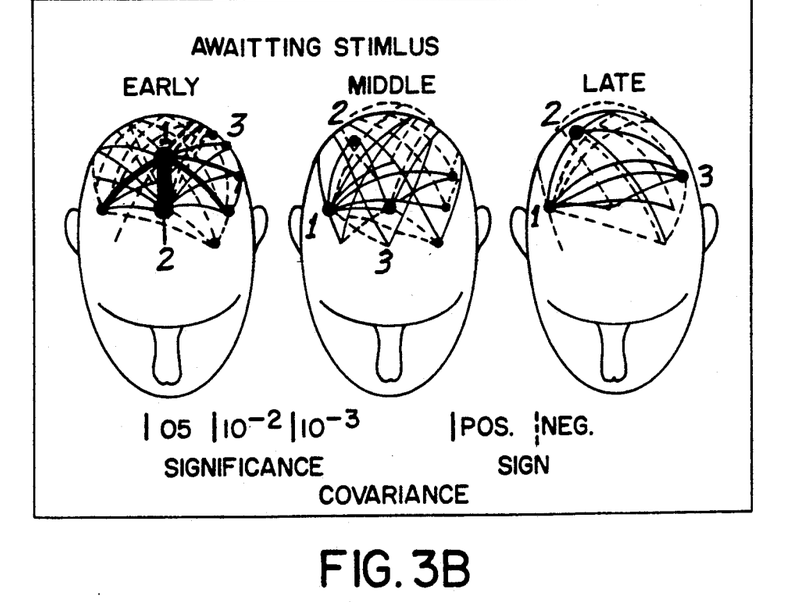
FIG. 3B are top head shapes illustrating event-related covariance (ERC) patterns associated with the chart of FIG. 3A.

FIG. 3A is a chart showing grand-average (over all 5 subjects), event-related potential (ERP) Laplacian wave forms of the midline central (Cz) electrode during a 700 msec interval when subjects were expecting the next VMMT stimulus. Accurate Early (594 trials, solid line), Middle (517 trials, dashed line), and Late epoch (394 trials, dotted line) averages are shown. The indicated prestimulus ERC interval was used for computing the event-related covariance patterns shown in B. The root-mean-square ERP amplitude of this interval did not significantly differ across Early, Middle and Late epochs.

FIG. 3B shows event-related covariance (ERC) patterns characterizing the prestimulus Early (left), Middle (center) and Late (right) epochs. The view is from above the head with the nose at the top of the figure. ERCs were computed from ERPs across the $-562$ to $-62$ msec prestimulus interval shown in A. The thickness of a line is proportional to the negative logarithm of the significance (from 0.000005 to 0.05) of the covariance between 2 electrodes. A solid line indicates a positive covariance (waves of same polarity), while a dotted line represents a negative covariance (waves of opposite polarity). The radius of the disk at each site is proportional to the sum of the absolute values of the significant ERCs in which that site participated. Not only did the ERC magnitude greatly decline from Early to Middle to Late epochs, but the ERC pattern also changed with the emphasis shifting from the midline central and precentral and left parietal sites to the right antero-central and parietal and left central sites.

Figure 4A:
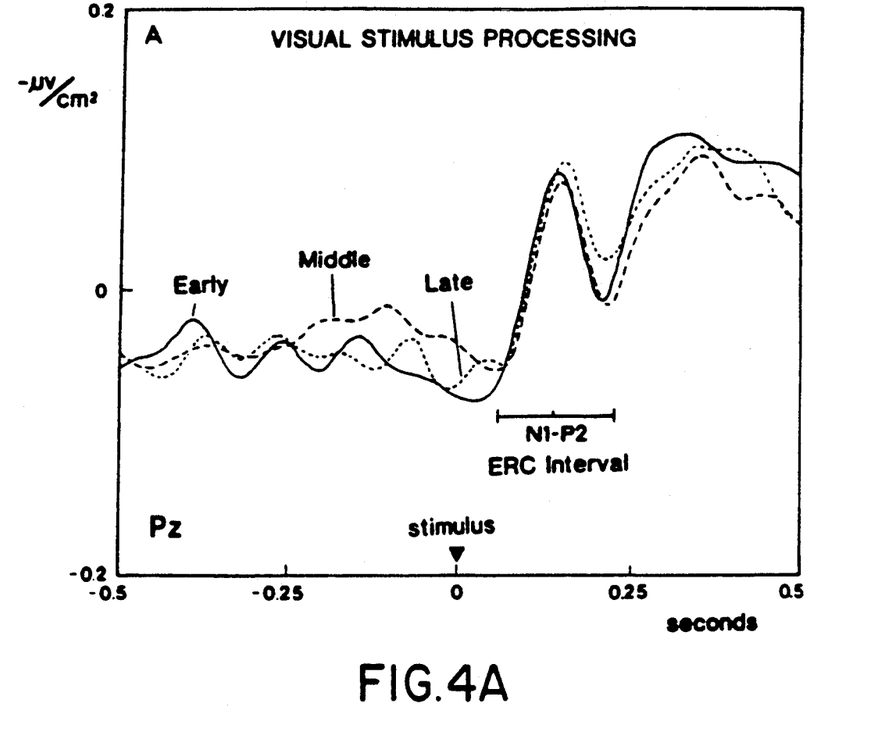
FIG. 4A is a chart showing grand-average ERPs at the midline parietal (Pz) electrodes during an interval a split-second later when subjects were processing a new number which just appeared on the screen.
Figure 5A:
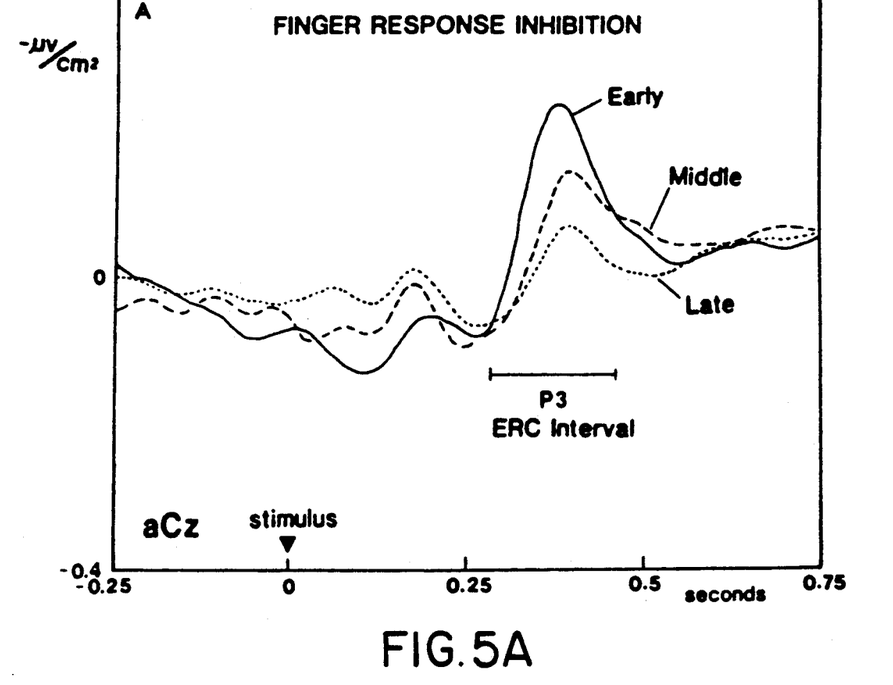
FIG. 5A is a chart showing grand-average ERP's at the midline precentral Cz electrode during the next split-second interval for those trials when the subjects had to inhibit their finger response.

FIG. 4A is a chart showing accurate early (562 trials, solid line), Middle (517 trials, dashed line) and Late (384 trials, dotted line) grand-average ERPs of the midline mid-arietal (Pz) electrode site, showing the N1-P2 interval following presentation of the visual stimulus. As in the pre-stimulus interval, the ERP amplitude did not differ significantly across the Early, Middle and Late epochs.

Figure 4B:
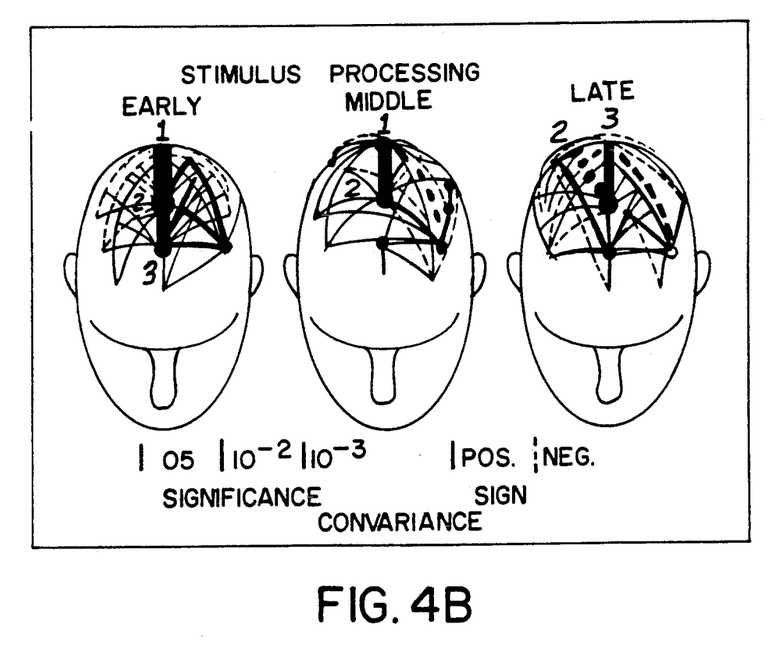
FIG. 4B are top head shapes illustrating ERC patterns associated with the chart of FIG. 4A.

FIG. 4B shows ERC patterns characterizing the post-stimulus N1-F2 interval in Early (left), Middle (center)

and Late (right) epochs. ERCs were computed from ERPs across the 187 msec long post-stimulus interval shown in FIG. 4A. The mean ERC magnitude changed only moderately from Early to Middle to Late epochs, the top focal sites remained nearly the same.

FIG. 5A is a chart showing accurate Early (243 trials, solid line), Middle (250 trials, dashed line), and Late (261 trials, dotted line), grand-average ERPs for the finger response inhibition ('No-press') trials, showing the P3 peak at about 380 msec after the stimulus at the midline antero-central (aCz) electrode site. The P3 amplitude declined from Early to Middle to Late epochs.

Figure 5B:
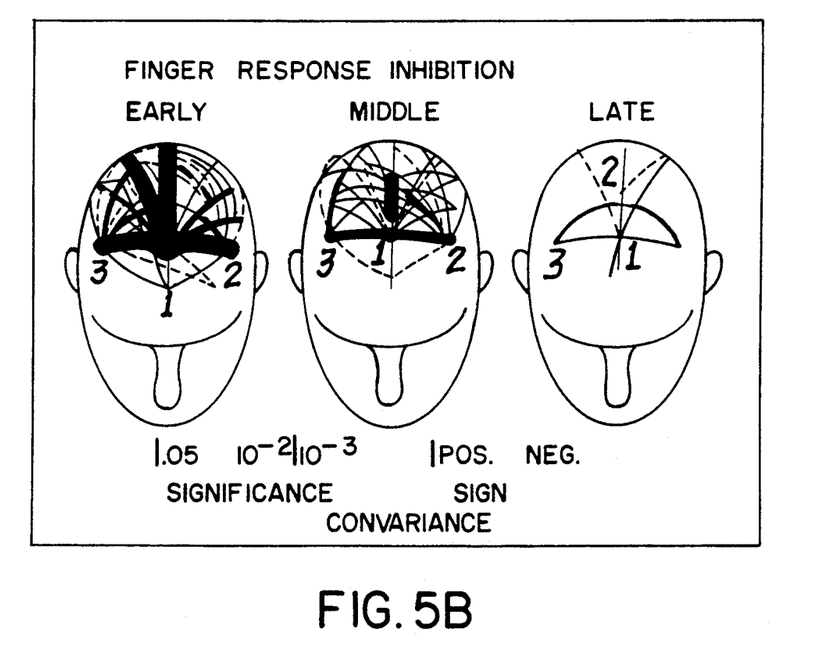
FIG. 5B are top head shapes illustrating ERC patterns associated with the chart of FIG. 5A.

FIG. 5B shows 'No-Press' ERC patterns characterizing Early (left), Middle (center), and Late (right) epochs. ERCs were computed from ERPs during the 281-468 msec post-stimulus interval shown in FIG. 5A. As in the prestimulus interval, there was a marked global decline in ERC magnitude. However, unlike the case in the prestimulus interval (but like the N1-P2 interval), the 3 patterns were very similar.

Statistical Evaluation

To measure functional changes in the brain strictly related to sustained mental work and unconfounded by variations in performance accuracy, we controlled for the significant effect of response error across the Early, Middle and Late epochs. The most stringent method was to analyze only the most accurate trials from each of the 3 epochs. We first selected the most accurate half of each subject's Early trials, and then selected trials with comparable accuracy from corresponding Middle and Late sets. Accurate trials were those with response error less than the mean response error of the Early trial set. We then discarded the least accurate outlier trials of the accurate Middle and Late subsets (roughly 2% of the trials) so that the final accuracy distributions of the three epochs did not significantly differ (P<0.2 by the Student's t test). The numbers of total trials in the resulting accurate trial sets were 599 (Early), 520 (Middle), and 402 (late) (FIG. 2). Measures of motor performance did not differ between these final accurate trial sets. We also selected, from all 3 epochs, No-Press trials in which the subjects correctly inhibited their response.

We determined the significance of Early, Middle and Late ERCs by referring to the standard deviation of the ERC 'noise' distributions obtained with a randomization procedure from the same trial sets. Significant ERCs were those with a probability of being less than 0.05 from the 'noise' distribution. ERC significances in each interval were displayed on computer graphic images of a model head; the thickness of a displayed ERC line is proportional to the negative log of significance. The relative involvement of each electrode site in an ERC pattern was determined by taking the sum of all significant ERCs in which it participated, and displaying at that site a disk whose size was proportional to the sum.

Analysis of variance (ANOVA) of the mean absolute ERC value (called ERC magnitude in Table I) provided an index of the change in mean level of between-site covariation over Early, Middle and late epochs. To compare any 2 epochs for differences in pattern configuration (called ERC pattern in Table I), the 2 patterns of significant ERCs were correlated. The ERCs in each set were pooled from the group of site pairs that had significant ERCs in either pattern. We used a distribution-independent 'Monte-Carlo' procedure to estimate correlations between patterns since we could not confirm that the data were normally distributed after examining the small number of repeated measures. To compare the significance of ERC magnitude differences with ERP amplitude differences, we tested the changes in root-mean-square amplitude over epochs for each ERP wave by ANOVA (ERP amplitude in Table I). Pairwise comparisons of ERC magnitude and ERP amplitude were performed by the Scheffe post-hoc procedure.

Results

Behavioral Analysis

By ANOVA, no significant differences were found between three 100-trial subsets at the beginning, middle and end of the Early epoch. This suggested that performance had asymptoted and that any subsequent performance degradation could be attributed to prolonged mental work. We observed that performance changed from Early to Middle to Late epochs (FIG. 2) with fewest errors occurring, as expected, in trials from the Early epoch. ANOVA revealed a significant increase in response error from Early to Late epochs (F (w,12)=12.5, P<0.005) (FIG. 2): Scheffe posthoc.

Comparisons revealed that the differences were significant between Middle and Late epochs (F (2.12)=4.8, P<0.05) but not between Early and Middle epochs. Reaction time did not differ across Early (543+/−169 msec), Middle (584+/−155 msec), and Late (593+/−97 msec) epochs. The increase in the proportion of responses during No-Press trials across the 3 epochs (10%, 16%, and 32%) was significant (F (2,12)=7.4, P<0.01).

Subjective reports were consistent with the trends in the behavioral data (Table II). Using a 7-level subjective fatigue scale (1 indicates maximal alertness and 7 complete exhaustion), the 5 subjects reported mean ratings of 3.42+/−0.75 during the Early epoch, 5.05+/−1.23 during the Middle, and 6.22+/−0.44 during the Late (F(2,12)=13.2, P<0.001). There was little correlation between the subjective fatigue ratings and response error (bootstrap correlation=−0.17+/−0.25).

ERC Analysis: Prestimulus Preparatory Interval

ERCs from the prestimulus interval declined in magnitude (F(2,243)=22.8, p<10$^{-9}$) and differed in pattern configuration across the 3 epochs (FIG. 3B and Table I). The greater change from Early to Middle epochs was revealed by the low Early-to-Middle bootstrap correlation (0.06) when compared to the Middle-to-Late one (0.42), and by the significant decline in Early-to-Middle ERC magnitude (F(2, 243)=11.2, P<0.0001) when compared to the non-significant Middle-to-Late difference. Dominance by the midline central (Cz) site in the Early epoch was replaced by right-sided dominance (focused at the right antero-central (aC4)site) in the Middle epoch, which continued into the Late epoch (Table III). The ERP amplitude in this interval declined by 15% from Early to Middle epochs and then rose by 3% in the Late epoch; the change over the 3 epochs was not significant.

ERC Analysis: Visual Stimulus Processing Interval

The amplitude of the poststimulus N1-P2 ERP component did not change with time-on-task (FIG. 4A and Table I, middle row). The mean absolute ERC magnitude declined form the Early (9.5+/−58) to Middle (7.5+/−4.5) epochs, but then rose in the Late (9.9+/−4.8) epoch. Although this change across the 3 epochs was significant (F(2, 225)=4.8 P<0.01), the effect was considerably less robust than for either the prestimulus CNV or subsequent P3 intervals. The Early and Middle ERC patterns (FIG. 4B) were similar (bootstrap correlation=0.71+/−0.09), and both had many features in common with the Late pattern. In particular, the midline pareital (Pz) and midline central (Cz) sites were among the top 3 focal sites in all 3 epochs (Table III). The Middle and Late patterns differed most (bootstrap correlation=0.44+/−0.14), largely because involvement of the right postero-parietal (pP2) site increased in the Late pattern.

ERC Analysis: Response-Inhibition Interval

ERCs from the poststimulus interval of No-Press trials declined greatly in magnitude (F (2, 231)=54.7, $P<10^{-10}$), but did not differ greatly in pattern configuration (Table I and FIG. 5B). There was also a significant decline in P3 amplitude (F (2, 51)=4.4, P<0.05). The stability of the pattern configuration was seen in the similarity between the Early-to-Middle and the Middle-to-Late bootstrap correlations, and by the dominance of the patterns by the antero-central sites in all 3 epochs (Table III). There are highly significant ERCs between these sites and the midline parietal (Pz) and right posterior parietal (pP2) sites.

Individual Subject Analysis

We next determined the extent of which individual subject patterns corresponded to the group patterns, and the extent to which it was possible to distinguish individual trials taken from different epochs of the session. Since the ERC patterns from the prestimulus intervals in the Early and Middle epochs were so strikingly different, we tested inter-subject variability on these data sets. Five equations were formed on four-fifths of the trials, and tested on the remaining one-fifth.

Discrimination was above 57% (P<0.05) for 3 subjects, but was 49% (chance) for the other two. Average test-set discrimination was 62% (P<0.001) for separate analyses of the first 3 subjects and 61% (P<0.001) for the latter two. Finally, a fourth analysis used only trials from the subject with the best classification in the 5- and 3-subject analyses. The average test-set discrimination was 81% (P<0.001). Thus, individual trials from the Early and Middle data sets could be distinguished with increased accuracy when the 5 subjects were divided into 2 groups, and for an individual subject.

Discussion

A fundamental theme in contemporary cognitive neuroscience is that mental function is composed of multiple information-processing subsystems associated with neural networks in the brain. The British neurologist Henry Head, an early 20th century proponent of this idea, considered that impaired 'vigilance' could cause "high-grade functions (to) suffer in general or in part,' and that neural systems could thus be affected either globally or selectively. We observed 2 major effects of sustained mental work that support Head's original ideas: (1) a global decrease in ERC magnitudes, consistent with the well-known spatially widespread reduction in neuroelectric signals with decreasing alertness and (2) a previously unreported, temporally specific change in ERC pattern configuration.

The prestimulus ERCs underwent a considerable change in pattern together with a large reduction in magnitude from the Early to Middle epochs. The poststimulus response inhibition ERC pattern strength was also reduced, but without much pattern change from Early to Middle and from Middle to Late epochs. Except for the emergence of the right postero-parietal site in the Late epoch the stimulus processing ERCs underwent relatively little change in ERC pattern or magnitude. These results suggest that specific cortical areas involved in response preparation were most affected by prolonged mental work and that those involved in response inhibition were also affected. Cortical areas involved in primary visual stimulus processing were considerably less affected.

Although the source of ERCs is still unknown, the recent results conform to the hypothesis that ERC patterns reflect underlying cortical networks. The prominence of the midline central and antero-central sites in the prestimulus interval is consistent with a cortical network component responsible for motor preparation, since these sites overlie the supplementary motor area (Brodmann area 6). The declining prominence of these sites over the 3 epochs may reflect decreasing involvement of the motor planning component with sustained mental work perhaps due to automatization. That these sites were also pronounced in the ERC pattern of the poststimulus N1-P2 interval suggests that this component remains in operation following the stimulus. Prominence of the midline parietal site may reflect a cortical network component concurrently involved in extracting the value of the stimulus from the visual image. In the poststimulus P3 interval, when subjects were inhibiting their response, the three antero-central sites largely dominated the patterns in all three epochs. These sites overlie supplementary and premotor areas, known to be necessary for higher other motor control such as response inhibition. The continued prominence of these sites in all 3 epochs suggests that these areas are critically involved in response inhibition, even as the strength of the pattern is reduced with sustained mental work.

Our findings also indicate that, since dramatic changes in brain activity patterns occurred before performance deteriorated significantly, measures of brain activity may be more sensitive indicators of the deleterious effects of sustained mental work than measures of overt behavior. This evidence could explain, in part, the increased vulnerability to life threatening accidents that exists during the early stages of prolonged mental activity, when performance has not yet become significantly degraded.

TABLE I

Significance of comparisons across Early, Middle, and Late epochs of the day for each of 3 neuroelectric measures in prestimulus, stimulus processing, and response inhibition intervals of the visuomotor memory task. For ERP amplitude and ERC magnitude, the Earyl vs. Middle vs. Late comparisons were preformed by analysis of variance, whereas the pairwise comparisons were performed by the Scheffe post-hoc method. Values are probabilities (P<) except in colums headed by 'ERC pattern' which are correlations between event-related covariance distributions. The standard deviation of correlation is shown in parentheses.

| Interval (msec) | ERP amp. | ERC magnitude | ERC pattern | ERP amp. | ERC magnitude | ERC pattern |
|---|---|---|---|---|---|---|
| | Early vs. Middle vs. Late epochs | | | Early vs. Middle epochs | | |
| Prestimulus (−562 to −62 msec) | NS | $10^{-9}$ | | NS | $10^4$ | 0.06 (0.09) |
| Stimulus processing (32-219 msec) | NS | 0.01 | | NS | 0.05 | 0.71 (0.09) |
| Response inhibition (282-469 msec) | 0.05 | $<10^{-10}$ | | NS | $10^8$ | 0.67 (0.09) |
| | Early vs. Late epochs | | | Middle vs. Late epochs | | |
| Prestimulus (−562 to −62 msec) | NS | $10^{-8}$ | 0.01 (0.09) | NS | NS | 0.42 (0.11) |
| Stimulus processing (32-219 msec) | NS | NS | 0.62 (0.07) | NS | 0.05 | 0.44 (0.14) |
| Response inhibition (282-469 msec) | 0.05 | $<10^{-10}$ | 0.66 (0.07) | NS | 0.0005 | 0.51 (0.16) |

TABLE II

Mean subjective fatigue ratings from each of the 3 epochs for the 5 subjects based on a 7-level subjective fatigue scale (1 indicates maximal alertness and 7 complete exhaustion).

| Subject | Early | Middle | Late |
|---|---|---|---|
| 1 | 3.51 | 5.00 | 6.12 |
| 2 | 4.12 | 6.00 | 6.00 |
| 3 | 3.20 | 5.25 | 6.00 |
| 4 | 4.00 | 6.00 | 7.00 |
| 5 | 2.25 | 3.00 | 6.00 |
| Mean | 3.42 | 5.05 | 6.22 |
| (S.D.) | (0.75) | (1.23) | (0.44) |

TABLE III

Sums of event-related covariances at top 3 sites in prestimulus, stimulus processing, and response inhibition intervals for Early, Middle and Late epochs of the day. Designation of sites is as follows: aC3 = left antero-central, aCz = midline antero-central, aC4 = right antero-central, C3 = left central, Cz = midline central, Pz = midline parietal, P4 = right parietal, pP1 = left postero-parietal, pP2 = right postero-parietal.

| Interval | | Early | | Middle | | Late | |
|---|---|---|---|---|---|---|---|
| Prestimulus | 1 | Cz | 624 | aC4 | 282 | aC4 | 235 |
| | 2 | aCz | 415 | P4 | 277 | P4 | 221 |
| | 3 | pP1 | 330 | aCz | 240 | C3 | 162 |
| Stimulus processing | 1 | Pz | 237 | Pz | 178 | Cz | 197 |
| | 2 | Cz | 200 | Cz | 140 | pP2 | 196 |
| | 3 | aCz | 173 | aC3 | 123 | Pz | 187 |
| Response inhibition | 1 | aCz | 574 | aCz | 284 | aCz | 103 |
| | 2 | aC3 | 360 | aC3 | 199 | Cz | 77 |
| | 3 | aC4 | 344 | aC4 | 186 | aC4 | 30 |

I claim:

1. A method to determine the mental performance capacity of a human subject to perform a work assignment, including the steps of:

(a) testing the subject in a test of performance of a task, while the subject is sober, alert and healthy, to obtain a normative test score for the subject and recording said normative test score;

(b) simultaneously with (a) detecting and analyzing the brain waves of the subject with an EEG (electroencephalograph) device having a plurality of electrodes removably connected to the scalp of the subject to determine a normative neurocognitive capacity score for the subject which is the normal neurocognitive capacity utilized by the subject to obtain the normative test score, and recording the normative neurocognitive capacity score; and subsequently (c) testing the subject in a test of performance of a task to obtain a test score and comparing the test score with the normative test score;

(d) simultaneously with (c) detecting and analyzing the brain waves of the subject with an EEG (electroencephalograph) device having a plurality of electrodes removably connected to the scalp of the subject to determine the neurocognitive capacity the subject used to pass the test of (c), and comparing said neurocognitive capacity used by the subject with the normative neurocognitive capacity score; and (e) rejecting the subject so that the subject does not perform the work assignment if the subject's test score of (c) is a predetermined passing score below the normative test score or if the subject's test score of (c) is above said passing score but the subject requires excessive neurocognitive capacity as determined in (d) to obtain the passing score.

2. A method as in claim 1 wherein the subject has a daily work assignment and the subject is tested according to steps (c), (d) and (e) each day prior to the subject's work assignment.

3. A method as in claim 2 and the subject is tested at least twice each day of work according to steps (c), (d) and (e).

4. A method as in claim 1 wherein the subject in steps (a) and (c) wears a hat having a plurality of electrodes to contact the scalp of the subject.

5. A method as in claim 1 wherein the tests of (a) and (c) use a display which is displayed on the screen of a digital computer system and are selected from the group of visuomotor memory tests, mathematical processing tests, logical reasoning tests, spatial processing tests, memory search tests, visuomotor tracking tests, divided attention lists, short term memory tests, word scramble tests, N-back working memory tests, N-back divided attention tests, attentional flexibility tests, driving simulation tests and flight simulation tests.

6. A method as in claim 5 wherein the subject responds to the trials by operation of a computer input peripheral device selected from the group of a pressure key, a mouse, a keyboard and a joystick.

7. A method to determine the mental capacity of a human subject to perform a work assignment, including the steps of:
   (a) testing the subject in a test of performance of a task, while the subject is sober, alert and healthy, to obtain a normative test score for the subject and recording said normative test score;
   (b) simultaneously with (a) detecting and analyzing at least one physiological function of the subject with a physiological monitoring device to determine a normative neurocognitive capacity score for the subject which is the normal neurocognitive capacity utilized by the subject to obtain the normative test score, and recording the normative neurocognitive capacity score; and subsequently
   (c) testing the subject in a test of performance of a task to obtain a test score and comparing the test score with the normative test score;
   (d) simultaneously with (c) detecting and analyzing said physiological function of the subject with a physiological monitoring device to determine the neurocognitive capacity the subject used to pass the test of (c), and comparing said neurocognitive capacity used by the subject with the normative neurocognitive capacity score; and
   (e) rejecting the subject so that the subject does not perform the work assignment if the subject's test score of (c) is a predetermined passing score below the normative test score or if the subject's test score of (c) is above said passing score but the subject requires excessive neurocognitive capacity as determined in (d) to obtain the passing score.

8. A method as in claim 7 wherein the subject has a daily work assignment and the subject is tested according to steps (c), (d) and (e) each day prior to the subject's work assignment.

9. A method as in claim 8 wherein the subject is tested at least twice each day of work according to steps (c), (d) and (e).

10. A method as in claim 7 wherein the subject in steps (a) and (c) wears a hat having a plurality of electrodes to contact the scalp of the subject.

11. A method as in claim 7 wherein the tests of (a) and (c) are visumotor memory task trials using a display which is displayed on the screen of a digital computer system.

12. A method as in claim 7 wherein the subject responds to the trials by operation of a computer input peripheral device selected from the group of a pressure key, a mouse, a keyboard and a joystick.

13. A method as in claim 7 wherein the physiological function is brain waves and the physiological monitoring device is an EEG (electroencephalograph) device.

14. A method as in claim 13 wherein an additional physiological function is detected and analyzed, said additional physiological function being selected from the group of eye activity, facial or scalp muscle potentials, heart activity, respiration and skin conductance.

15. A method as in claim 7 wherein the said physiological function is selected from the group of eye activity, facial or scalp muscle potentials, heart activity, respiration and skin conductance.

16. A method to track the mental capacity of a human subject over time as an indication of brain functioning, including the steps of:
   (a) testing the subject in a test of performance of a task while the subject is sober and alert at a first date to obtain a normative test score for the subject and recording said normative test score;
   (b) simultaneously with (a) detecting and analyzing at least one physiological function of the subject with a physiological monitoring device to determine a normative neurocognitive capacity score for the subject which is the normal neurocognitive capacity utilized by the subject to obtain the normative test score, and recording the normative neurocognitive capacity score; and subsequently, at a later date;
   (c) testing the subject, while the subject is sober and alert, in a test of performance of a task to obtain a test score and comparing the test score with the normative test score;
   (d) simultaneously with (c) detecting and analyzing said physiological function of the subject with a physiological monitoring device to determine the neurocognitive capacity of the subject used to pass the test of (c), and comparing said neurocognitive capacity used by the subject with the normative neurocognitive capacity score; and
   (e) determining, as an indication of the mental functioning of the subject, if the subject's test score of (c) is a predetermined passing score below the normative test score or if the subject's test score of (c) is above said passing score but the subject requires excessive neurocognitive capacity as determined in (d) to obtain the passing score.

17. A method as in claim 16 wherein the subject in steps (a) and (c) wears a hat having a plurality of electrodes to contact the scalp of the subject.

18. A method as in claim 16 wherein the tests of (a) and (c) are visumotor memory task trials using a display which is displayed on the screen of a digital computer system.

19. A method as in claim 16 wherein the physiological function is brain waves and the physiological monitoring device is an EEG (electroencephalograph) device.

20. A method as in claim 19 wherein an additional physiological function is detected and analyzed, said additional physiological function being selected from the group of eye activity, scalp or facial muscle potentials, heart activity, respiration and skin conductance.

21. A method as in claim 16 wherein the said physiological function is selected from the group of eye activity, scalp or facial muscle potentials, heart activity, respiration and skin conductance.

22. A system to determine the mental capacity of a human subject to perform a work assignment, including
   (a) testing means for testing the subject in the test of performance of a trial to obtain a test score and digital computer means to compare the obtained test score with a recorded normative test score obtained from performance testing the subject while the subject was sober, alert and healthy;
   (b) physiological monitoring means for detecting and analyzing at least one physiological function of the subject to determine the neurocognitive capacity the subject uses while taking the trial of (a); wherein the physiological monitoring device includes a device selected from the group of an EKG heart monitor, and EMG muscle monitor, a skin conductivity monitor, and an electro-optical eye movement and blink sensor and an electrical eye movement and blink sensor; and (c) comparison computer means to automatically compare the neurocognitive capacity used by the subject as determined by the EEG means with a recorded normative neurocognitive capacity score obtained by an EEG device connected to the subject while the subject was sober, alert and healthy;

whereby the comparisons of (a) and (c) are used to determine if the subject's test score of (a) is below a passing grade based on the normative test score or if the subject's test score of (a) is above said passing grade and whether the subject required excessive neurocognitive capacity as determined by the computer comparison means of (b) to obtain the passing grade.

* * * * *